United States Patent [19]

Nagata et al.

[11] 4,180,626

[45] Dec. 25, 1979

[54] PROCESS FOR MANUFACTURING CITRIC ACID FROM OLEFINS BY FERMENTATION

[75] Inventors: Takeo Nagata, Yokohama; Seisuke Satoh; Takao Matsumoto, both of Tokyo, all of Japan

[73] Assignee: Showa Oil Co., Ltd., Tokyo, Japan

[21] Appl. No.: 865,397

[22] Filed: Dec. 29, 1977

[30] Foreign Application Priority Data

Feb. 25, 1977 [JP] Japan .................................. 52-19285
Feb. 25, 1977 [JP] Japan .................................. 52-19286

[51] Int. Cl.$^2$ .............................................. C12D 1/04
[52] U.S. Cl. ..................................... 435/144; 435/924
[58] Field of Search ............................... 195/37, 28 R

[56] References Cited

U.S. PATENT DOCUMENTS

| 3,873,424 | 3/1975 | Kimura et al. | 195/37 |
| 3,902,965 | 9/1975 | Furukawa et al. | 195/28 R |
| 4,014,742 | 3/1977 | Nubel | 195/28 R |

FOREIGN PATENT DOCUMENTS 7115848  5/1972 Netherlands .............................. 195/37

*Primary Examiner*—Lionel M. Shapiro
*Attorney, Agent, or Firm*—Oldham, Oldham, Hudak & Weber Co.

[57] ABSTRACT

The present invention relates to a microbiological process for the production of citric acid by assimilation of olefins. Normal olefins of $C_{8-40}$ produced from thermal cracking of petroleum wax or from polymerization of ethylene are suitable as carbon source for this fermentation process. Said process is carried out by culturing the microorganism selected from the group of *Candida tropicalis*, *Candida intermedia* and *Candida brumptii*, their mutants and their variants in the culture medium containing acid olefins. Citric acid is accumulated in said medium in the process of the culture.

The most suitable strain utilized in the present invention is *Candida tropicalis*, their mutants and their variants.

7 Claims, No Drawings

PROCESS FOR MANUFACTURING CITRIC ACID FROM OLEFINS BY FERMENTATION

BACKGROUND OF THE INVENTION

The present invention relates to a fermentation process for production of citric acid from olefins. It has been well known that citric acid is produced by the assimilation of normal paraffins of $C_{12-18}$ as carbon source to culture microorganisms.

Furthermore, it has been attempted to use paraffin wax as carbon source for the fermentation of hydrocarbons. But paraffin wax is in a solid state at fermentation temperature usually 25° to 35° C. It is necessary for the fermentation process to disperse the carbon source in the form of microparticles or to dissolve it in the culture medium. Then, many surface active agents were applied to improve the dispersion property of solid wax by many investigators for number of years. But the application of surface active agents is not completely adopted, because their dispersibility only displays in the concentration of about 3 percent weight of surface active agents to the culture medium; surface active agents hinder frequently the productivity of citric acid in cultivation; and the dispersibility of surface active agents is reduced by their rapid assimilation.

Taking it into consideration, the melting point of olefin is lower than the same carbon number of normal paraffin, the dispersion of olefins, especially having the carbon number more than 8, is superior to that of normal paraffins. On the background mentioned above, we, inventors, have made efforts to develop the fermentation process for the production of citric acid by assimilation of olefins.

Olefins less than the carbon number of $C_{13}$ are in great demand as the raw materials for plasticizers and for synthetic detergents. However, olefins more than 14 are not in demand in the market and the present invention provides one of the profitable way of promoting the effective utilization of such olefins.

One of characteristic features of the present invention lies in the use of mixture of crude olefins as carbon source in the culture medium. As the mixture of crude olefins produced from thermal cracking of crude paraffin wax may be used as carbon source, the cost of the carbon source becomes cheaper. Therefore, the application of crude olefins for the process of the present invention is useful for the reduction of citric acid manufacturing cost.

SUMMARY OF THE INVENTION

The main object of this invention is to provide a manufacturing process of citric acid by culturing the olefin assimilable microorganisms in culture medium containing olefins under aerobic conditions.

The above object is accomplished by cultivating of the microorganism selected from the group of *Candida tropicalis*, *Candida intermedia* and *Candida brumptii* in the culture medium containing any olefin of $C_{8-40}$ as carbon source. Especially, the most suitable microorganism utilized to the process of this invention is the strain belonging to *Candida tropicalis* and its auxotrophic mutants and its variants. Also, mixture of olefins may be used as carbon source for the fermentation process in this invention. The carbon number of olefins in said mixture is in the range of 8 to 40 in normal α-olefin form. But some iso- and inner olefins are allowed in normal α-olefins.

Most suitable olefins are olefins of $C_{8-40}$, especially $C_{14-40}$ olefins which are not marketable at present. Mixture of these olefins is produced from thermal cracking of crude petroleum wax and from polymerization of ethylene. Said mixture can be held in liquid state at fermentation temperature of about 30° C., in which good dispersion of said mixture of olefins in the culture medium can be maintained. The concentration of said olefins in the culture medium is 1 to 20 percent weight, preferably 5 to 15 percent weight.

As the nitrogen source of the culture medium, inorganic and organic ammonium salts, such as ammonium chloride, ammonium acetate, and various nitrogen compounds may be used individually or in mixture.

Ordinary inorganic salts such as phosphate, sulfate, hydrochloric acid salts, potassium salts, sodium salts, magnesium salts, iron salts, managanese salts, cooper salts and Zinc salts may be used as inorganic nutrients in culture medium. Calcium carbonate and alkali compounds may be used to regulate pH of said medium. Biotin and thiamine as organic nutrients may be used in a trace amount individually or in their mixture, and also natural substances such as yeast extract or corn steep liquor containing biotin and thiamine may be used. When biotin and thiamine are used individually, the amount less than 1,000 μg/l of biotin or thiamine suffices to increase the production amount of citric acid. Even if the amount more than 1,000 μg/l of biotin or thiamine is used individually, the production amount of citric acid does not increase. Preferable amount of the organic nutrients is suitable from 50 to 100 μg/l. In case where both biotin and thiamine are added in said medium, the total amount of biotin and thiamine less than 1,000 μg/l, preferably 50-100 μg/l is enough to cultivate. During process of this invention, α-olefin or mixture of olefins may be used as carbon source. These substrates are in liquid state at fermentation temperature. Thus any surface active agent which hinders the cultivation activity of microorganism is not necessary.

Details of the invention are as follows.

Said microorganism are cultivated under aerobic conditions. The fermentation temperature is in the range of 25° and 40° C., preferably about 30° C. pH value of said medium is in the range of 3–10, preferably 4–6. pH value of said medium is regulated by adding alkalis or salts such as sodium carbonate or calcium carbonate. The cutivation is ordinarily carried out for 50-150 hrs., preferably 80-100 hrs. Citric acid accumulated in said medium is isolated in the form of calcium citrate by normal method, for example, by filteration or by centrifugal method and then purified by chromatographic or ion exchange method.

DETAILED DESCRIPTION OF THE INVENTION

Manufacturing process for citric acid which culture many microorganisms in the culture medium containing normal paraffins (n-$C_{12-18}$) as carbon source are well known.

Thus, for the purpose of understanding the assimilability of olefins by well known microorganisms, the growth of said microorganisms on inorganic slant culture medium containing olefins was observed. Said inorganic slant culture medium consisted of following ingredients;

| | |
|---|---|
| NH$_4$Cl | 5.0g |
| Na$_2$HPO$_4$.12H$_2$O | 1.5g |
| KH$_2$PO$_4$ | 3.5g |
| MgSO$_4$.7H$_2$O | 0.5g |
| FeSO$_4$.7H$_2$O | 10mg |
| MnSO$_4$.7H$_2$O | 0.1mg |
| ZnSO$_4$.7H$_2$O | 0.1mg |
| CuSO$_4$.5H$_2$O | 5 g |
| Biotin | 100μg |
| Thiamine.HCl | 100μg |
| Agar | ca.20g |
| Taped water was used as solvent. | |
| pH | 5.0 |
| 115° C., 10 min. sterilization | |
| α-olefin | 0.5ml/slant |

Microorganisms were cultured on said slant at 30° C. for 3 days. Cultivation results are shown in table 1.

The microorganisms shown in table 1 have been well known as the strains producing citric acid from normal paraffins.

Table 1

Cultivation results of the various kinds of microorganisms on the inorganic slant culture medium

| Kinds of microorganisms | IFO - No. | carbon source | |
|---|---|---|---|
| | | n-Octa-decane | n-α-olefins ($C_{16-30}$) |
| Candida tropicalis | 0589 | +++ | +++ |
| Candida intermedia | 0761 | + | + |
| Candida brumptii | 0744 | ++ | + |
| Candida lipolytica | 0746 | +++ | + |
| Candida guilliermandii | 0838 | + | + |
| Pichia ohmeri | 1374 | + | − |
| Debaryomyces hansenii | 0019 | + | ± |

Note:
+++ very good growth;
++ good growth;
+ moderate growth;
± very feeble growth;
− no growth.
(IFO; Institute of Fermentation, Osaka, Japan)

From the results of preexperimental works as shown in table 1, we, inventors, have completed the present invention for the manufacturing process of citric acid from $C_{8-40}$ olefins by fermentation. Hereinafter are described the examples of the present invention. The process of the present invention is not to be limited to the following examples.

Example 1

(1) Fermentation

| The compositions of the cultivation medium | |
|---|---|
| Kinds of Ingredients | Contents in 1 liter of culture medium |
| Normal octadecene-1 (n-$C_{18}$=-1) | 100g |
| NH$_4$Cl | 3.0g |
| KH$_2$PO$_4$ | 0.5g |
| MgSO$_4$.7H$_2$O | 0.3g |
| FeSO$_4$.7H$_2$O | 5mg |
| MnSO$_4$.H$_2$O | 0.06mg |
| ZnSO$_4$7H$_2$O | 0.05mg |
| CuSO$_4$.5H$_2$O | 5μg |
| Biotin | 50μg |
| Thiamine.HCl | 100μg |
| [pH | 5.0] |

The seed of microorganisms described below was inoculated in 500 ml Erlenmeyer flasks containing 30 ml of said medium which was sterilized at 115° C. for 10 minutes and allowed to cool at 30° C. Said seed containing a strain belonging to Candida tropicalis, Candida brumptii, Candida lipolytica, Candida guilliermandii, Pichia ohmeri and debaryomyces hansenii was inoculated on said medium in the amount of 3 platinum wire loops respectively. The cultivation was carried out at 30° C. on a reciprocating shaker operating at 120 oscillis/minute with 7 cm stroke for 3 days. After about 20 hrs. from the beginning of the cultivation, 5% wt. of the freshly sterilized calcium carbonate was added into said medium to regulate pH 5.5.

(2) Recovery

Citric acid produced during the cultivation as described above was recovered in calcium salt form by filtering said medium using diatomaceous earth as a filter aid after conditioning pH to 2.5 with hydrochloric acid. The filter cake was washed with water and the washing water was combined with the clear filtrate and then heated after neutralizing the combined filtrate by caustic alkali. The combined filtrate was cooled and filtrated under the reduced pressure to recover calcium citrate. Calcium citrate produced was suspended into about 10 volume of water, and heated in the boiling water for about 30 minutes after titrating with 50% of aqueous sulfuric acid solution until the filtrate slightly indicates the presence of sulfuric acid anion with addition of the aqueous solution of barium chloride to said filtrate. If necessary, the resulting solution is filtered while heating after decoloring said filtrate and concentrated under the reduced pressure at 50°-60° C. During concentrating said filtrate, the precipitated calcium sulfate was filtered and continued to the concentration until the slightly washy syrup was obtained. When the syrup-like concentrated liquor allowed to cool at 0° C., the crystalline of citric acid was obtained.

The amount of citric acid are shown as follows;

| strains | amount of citric acid |
|---|---|
| Candida tropicalis | 59.5 g/l - culture medium |
| Candida intermedia | 5.0 g/l - culture medium |
| Candida brumptii | 5.5 g/l - culture medium |
| Candida lipolytica | trace |
| Candida guilliermandii | trace |
| Pichia ohmeri | trace |
| Debaryomyces hansenii | trace |

Example 2

The cultivation was carried out according to the method of Example 1. Candida Tropicalis IFO-0589 was cultivated in said medium containing the following ingredients as carbon source.

| | composition | |
|---|---|---|
| n-$C_{17}$=-1 | 5.3 | vol.% |
| n-$C_{18}$=-1 | 44.3 | " |
| n-$C_{19}$=-1 | 1.7 | " |
| n-$C_{20}$=-1 | 44.3 | " |
| n-$C_{22}$-1 | 4.4 | " |

The amount of citric acid was 60.7 g/l-cultivation medium.

Example 3

The cultivation was carried out in said medium containing the mixture of normal olefins of $C_{16-30}$ produced from polymerization of ethylene by Ziegler's process under the same conditions as Example 1. Culture medium was the same as Example 1 except vitamins. To examine the requirement of vitamins to the cultivation, 100 μg of biotin and thiamine was added to 1 l of said medium respectively. While 100 μg of the mixture of biotin and thiamine-hydrochloric acid salt was added to 1 l of said medium. *Candida tropicalis* IFO-0589 was used in this example. The cultivation was continued for 140 hrs. The amount of citric acid was 61.5 g/l-said medium containing biotin only and the joint use of biotin and thiamine-hydrochloric acid salt respectively, while it came to 48.4 g/l-said medium containing thiamine-hydrochloric acid salt only.

Example 4

10 wt.% of the olefin mixture of $C_{10-35}$ produced from wax by thermal cracking was added to the culture medium consisting of following ingredients.

| | contents in 1 liter of culture medium |
|---|---|
| $NH_4Cl$ | 3g |
| $KH_2PO_4$ | 0.5g |
| $MgSO_4 \cdot 7H_2O$ | 0.3g |
| $FeSO_4 \cdot 7H_2O$ | 5mg |
| $MnSO_4 \cdot H_2O$ | 0.06mg |
| $ZnSO_4 \cdot H_2O$ | 0.05mg |
| $CuSO_4 \cdot 5H_2O$ | 5μg |
| Biotin | 50μg |
| Thiamine . HCl | 100μg |
| [pH | 5.0] |

*Candida tropicalis* IFO-0589, IAM-4185 and IAM-12202 were inoculated in said medium in the amount of 3 platinum wire loops respectively. The cultivation was carried out according to those of Example 1.

The amount of citric acid was shown as follows;

| strains | amount of citric acid |
|---|---|
| *Candida tropicalis* IFO-0589 | 61.5 g/l-said medium |
| *Candida tropicalis* IAM-4185 | 40.5 g/l-said medium |
| *Candida tropicalis* IAM-12202 | 45.4 g/l-said medium |

The compositions of crude olefins produced from crude wax by thermal cracking are shown as follows;

| | composition |
|---|---|
| n-α-olefin (n-$C_{10}$=-l-n-$C_{35}$=-1) | 73.38 wt % |
| iso-olefins and inner olefins | 17.10 wt % |
| n-paraffins (n-$C_{20}$ -n-$C_{37}$) | 9.52 wt % |

Example 5

Fermentation by use of jar was carried out in the culture medium containing the mixture of normal olefins of $C_{16-30}$ produced from polymerization of ethylene by Ziegler's process. The seed of *Candida tropicalis* IFO-0589 was cultivated at 30° C. for 70 hrs. in said medium as described in Example 1 prior to the above method. 65 ml of that seed and 163 ml of α-olefins described above were added to 2.6 l-jar fermentor containing 1072 ml of the same medium as described in Example 1. The cultivation was carried out for 3 days under the conditions at 30° C., 1,000 r.p.m. and 0.5 VVM-aeration, maintaining pH of said medium to 5.0 during the cultivation period by injection of 10 N-caustic soda aqueous solution. The amount of total citric acid was 126 g/l-said medium, and the yield of total citric acid to said α-olefin feed was 126 wt.%.

What is claimed is:

1. A process for producing citric acid by fermentation which comprises:
    culturing olefin assimilable microorganisms comprising *Candida tropicalis* under aerobic conditions at a temperature from about 25° C. to about 40° C. and at a pH from about 3 to about 10 in an aqueous nutrient medium containing olefins, selected from the group consisting of normal olefins having from 8 to 40 carbon atoms and combinations thereof, as the main carbon source together with less than 1,000 g/l of a vitamin selected from the group consisting of biotin or biotin and thiamine-hydrochloric acid.

2. The process according to claim 1, wherein the assimilable carbon source is the mixture of crude olefins of $C_8$–$C_{40}$ produced from thermal cracking of petroleum wax under the conditions of cracking temperature of 500°–650° C., of the liquid space velocity of 1–10 L.H.S.V., and of the molar ratios of water/wax of 5–10.

3. the process according to claim 1, wherein the assimilable carbon source is the mixture of normal olefins of $C_{8-40}$ produced from polymerization of ethylene.

4. The process according claim 1, wherein the amount of olefins added as the carbon source to the culture medium is 1–20% on the weight basis of said medium.

5. The process according to claim 2, wherein the amount of olefins added as a carbon source to the culture medium is 1-20 percent on the weight basis of said medium.

6. The process according to claim 3, wherein the amount of olefins added as a carbon source to the culture medium is 1-20 percent on the weight basis of said medium.

7. The process according to claim 1, wherein said *Candida tropicalis* is selected from the group consisting of *Candida tropicalis* IFO-0589, *Candida tropicalis* IAM-4185, and *Candida tropicalis* IAM-12202.

* * * * *

UNITED STATES PATENT OFFICE
CERTIFICATE OF CORRECTION

Patent No. 4,180,626          Dated December 25, 1979

Inventor(s) Takeo Nagata, Satoh Seisuke and Takao Matsumoto

It is certified that error appears in the above-identified patent and that said Letters Patent are hereby corrected as shown below:

Column 2, line 44, change "microorganism" to --microorganisms--.

Column 2, line 19, change "cooper" to --copper--.

Column 3, line 2, the heading --Contents in 1 liter of said medium-- should appear over the righthand column in the table of ingredients.

Signed and Sealed this

Sixth Day of May 1980

[SEAL]

*Attest:*

SIDNEY A. DIAMOND

*Attesting Officer*     *Commissioner of Patents and Trademarks*

UNITED STATES PATENT OFFICE
CERTIFICATE OF CORRECTION

Patent No. 4,180,626    Dated December 25, 1979

Inventor(s) Takeo Nagata, Seisuke Satoh and Takao Matsumoto

It is certified that error appears in the above-identified patent and that said Letters Patent are hereby corrected as shown below:

Column 6, line 30, after the number "1,000" correct "g/l" to --ug/l--.

Signed and Sealed this

Ninth Day of February 1982

[SEAL]

Attest:

GERALD J. MOSSINGHOFF

Attesting Officer    Commissioner of Patents and Trademarks